United States Patent [19]

Rothstein

[11] Patent Number: 4,485,439

[45] Date of Patent: Nov. 27, 1984

[54] STANDARD HARDWARE-SOFTWARE INTERFACE FOR CONNECTING ANY INSTRUMENT WHICH PROVIDES A DIGITAL OUTPUT STREAM WITH ANY DIGITAL HOST COMPUTER

[75] Inventor: Robert Rothstein, Dallas, Pa.

[73] Assignee: S.A. Analis, Namur, Belgium

[21] Appl. No.: 402,385

[22] Filed: Jul. 27, 1982

[51] Int. Cl.³ .............................................. G06F 3/00
[52] U.S. Cl. ................................................. 364/200
[58] Field of Search ........................ 364/200 MS File

[56] References Cited

U.S. PATENT DOCUMENTS

| 3,673,576 | 6/1972 | Donaldson | 364/200 |
| 4,052,702 | 2/1983 | Smith . | |
| 4,127,896 | 2/1983 | Raslavsky . | |
| 4,377,843 | 3/1983 | Garringer et al. | 364/200 |

FOREIGN PATENT DOCUMENTS

| 1419207 | 2/1983 | United Kingdom . |
| 1486362 | 2/1983 | United Kingdom . |
| 1594131 | 2/1983 | United Kingdom . |
| 2031194 | 2/1983 | United Kingdom . |

Primary Examiner—Raulfe B. Zache

Attorney, Agent, or Firm—Howard L. Rose

[57] ABSTRACT

A microprocessor-controlled interface for permitting any digital host computer to receive serial digital data from any instrument wherein (a) the time at which digital data from the instrument is to enter the host computer and (b) the logical structure of the digital data entering the host computer are controlled by instructions from the host computer to the microprocessor and wherein (a) physical formatting incompatabilities between the host computer and the instrument and (b) the communicating of prohibited characters from the instrument to the host computer and vice versa are avoided. The timing control and logical structure of the digital data are effected by directing data from the instrument into a scratchpad memory, which is divided into records pursuant to instructions from the host computer, the contents of the scratchpad memory being sent to the host computer upon a corresponding instruction therefrom. A terminal for communicating with the host computer and the instrument may be included. Physical formatting discrepancies are avoided by translating inputs to the interface into a common physical format and translating outputs from the interface into the physical format of the instrument, host computer, or terminal which is receiving such outputs.

48 Claims, 6 Drawing Figures

4,485,439

STANDARD HARDWARE-SOFTWARE INTERFACE FOR CONNECTING ANY INSTRUMENT WHICH PROVIDES A DIGITAL OUTPUT STREAM WITH ANY DIGITAL HOST COMPUTER

FIELD OF THE INVENTION

The invention relates to the connection of data acquisition apparatus to computer systems in general, and particularly to the connection of automated laboratory apparatus to clinical laboratory and/or hospital information systems.

TECHNOLOGICAL CONTEXT OF THE INVENTION

Computer-aided experimentation, in which data outputs from a laboratory device are processed or handled by a computer, has become particularly significant over the last twenty years. Particularly in the biological and medical fields, experiments which were previously difficult, if not impossible, to perform have become practical when the power of data processing has been added. Specifically, biological analyses of large numbers of specimens being tested can, with the aid of a computer, be processed in a short period of time.

As automation has become a key part of scientific and other experimentation, various problems were identified. In the 1960's, it was recognized that the vast majority of instruments provided analog output which was found to be relatively unstable. The computer was thus required to handle many data reduction functions. This problem has been resolved by including a minicomputer or microcomputer in the instrument itself. The instrument thus provides more reliable, sophisticated, and processed digital data-thereby relieving the host computer of various, previously required functions.

However, although the analog output and data reduction problems were resolved by refining the instrument, a new problem remained. Instrument and computers are often incompatible.

Although some standardization of instrument output has been achieved--e.g. most instruments having RS-232, RS-422, or IEEE 488 and asynchronous ASCII physical formats--not all instruments and computers follow any single physical data format. In addition, the logical structuring of output data into a particular form or layout and the timing of the output data still remain different from instrument to instrument. Further, different computers operate under different operating systems. In some computers for example, certain characters, when received, provide a special effect--such as a control function--which may be unintended when the data character is received from an instrument. Thus, instruments and computers can have any of various incompatable (a) physical formats, (b) data arrangement or logical structures, (c) timing schemes, and (d) "prohibited" characters.

In the past, highly diversified and customized ad-hoc solutions have been suggested to address some of the problems of nonstandardization. In such approaches, laboratory instrument A would be connected to computer system B operating under operating system C. Different hardware or, at least, a reprogramming would be necessary if any one of A, B or C changed, or if the operator wished to examine the output from the instrument in a particular logical structure or arrangement. That is, if the operator desired to collect data from the instrument in the form of a plurality of records of given size or dimensions, there was no simple practical way to do this.

In addition, little provision was made in prior schemes for operator intervention in the process of data communication. Of particular importance, the operator had no control over when data from an instrument was to be sent to the computer. If the computer was busy when data was sent by the instrument, the computer would have to be interrupted in time or the computer would continue without interruption ignoring the data being communicated from the instrument.

The significance of these problems is particularly amplified in the medical and biological research fields. In these fields the cost of instruments--due to the tasks performed and requirements imposed--is relatively high. Because such instruments are not replaced often, the flexibility of using such instruments readily with various computers and of varying the form in which the output is received has been a desirable end which, with the prior technology, has remained unachieved and unachievable.

Also aggravating the prior art problem of inflexibility, or inability to adapt instrument to computer, are several industry-related considerations: (1) manufacturers of instruments generally do not allow users to modify the original equipment hardware or software--so that the user cannot change the instrument to fit his computer; (2) users are generally reluctant to modify computer system software or develop special interfaces; and (3) users would prefer to avoid customized solutions wherein each type of laboratory instrument or method of logically structuring the data output from the instrument necessitates the writing of a special assembly language handler.

In sum, prior techniques of interfacing instruments and computers have not permitted any instrument providing serial digital outputs to be readily interfaced with any computer. Further, prior interfaces have not permitted user control whereby the logical structure of the data entering the computer and the timing of the input of data to the computer are user or computer controlled. Finally, the prior interfaces do not suggest modular hardware for allowing interfacing regardless of the physical format (or protocol) of the instrument or computer.

SUMMARY OF THE INVENTION

The present invention overcomes the problems of the prior technology by providing an instrument-host computer interface comprising (a) a microprocessor having an executive portion which executes instructions communicated to the microprocessor from the host computer and (b) a scratchpad memory which buffers data enroute to the host computer from the instrument.

In accordance with the invention, one set of instructions effects a division of the scratchpad memory into records. Another instruction effects the transfer of data from the instrument into the scratchpad memory, while still another instruction directs the data, which is logically structured into records in the scratchpad memory, to the host computer. It can thus be seen that it is an object of the invention to provide temporary storage of data from the instrumemt in a defined logical structure, with the data being forwarded to the host computer at any time during or after the instrument has transmitted it.

In a specific embodiment of the invention, a terminal is provided whereby the operator can communicate with the instrument or the host computer. When a communication channel between the terminal and the host computer is open, duplex communication may be entered into with normal interchanges. Further, the terminal and host computer may communicate as data from the instrument enters the scratchpad memory. It is thus an object of the invention to provide communication to and from the terminal in a manner fully transparent to the interface. The operator communicates with the host computer as if he were using any other host computer terminal. The result of this communication and its effect on the instrument, via the interface, depends solely on the user's, or operator's, programming of the host computer.

It is another object of the invention to overcome interfacing problems relating to differences in the physical formats of the computer and instrument (and terminal, if included). Specifically, all outputs from the computer and instrument (and terminal, if included) are translated, if necessary, to a standard physical format, such as asynchronous RS232. The interface thus reduces all data entering it to the standard physical format. Data exiting the interface is changed, if necessary, to the physical format compatable with the element to which the exiting data is destined.

In order to prevent the transmission of a character representing data at the instrument but representing a control or other prohibited character at the computer, a data convertor is provided between the instrument and the scratchpad memory. The convertor recognizes such a character and transforms it into a character representing to the computer the data intended to be transmitted by the instrument. Such a convertor is quite simple in nature and greatly increases the flexibility of the system.

For the various instruments and host computers (and terminals, if included), differing physical format translators and differing character convertors may be required. Because physical formatting is somewhat standardized--as previously noted--90% of the translations from one physical format to a common physical format, and vice versa, may be achieved by using one of three physical format translators. The instructions to the microprocessor which effect execution of the various operations underlying the data transfer remain at least substantially the same. In addition, unlike prior art solutions, neither the instrument nor the host computer not system software thereof need be changed in accordance with the invention.

It is thus an object of this invention to allow an operator at a terminal or host computer to customize the manner in which the computer system handles the data from or to an instrument (a) without any changes to the host computer or to the instrument; (b) without any changes to the operating system of the host computer; and (c) without any necessity for programming in a low-level language.

It is yet a further object of this invention to provide a universal, standard apparatus and method to present the output of any data acquisition device, and in particular, any laboratory instrument to a host computer. In accordance with the invention, the interfacing of instruments to host computers and terminals is remarkably facilitated. Specifically, three types of common translators are definable which, together, can perform necessary translations for approximately 90% of all current host computers (and instruments). For any specific instrument, all that need be done is to select one of the three defined translations for each physical format translator--wherein the three common translator types may be incorporated on a single card from which one of the three may be selected--and if necessary, the code converting for the instrument-host computer may be added. The code convertor for the instrument is preferably an EPROM. Thus, rather than designing a new and distinct interface for each instrument and host computer set-up as in the prior art, one embodiment of the present interface generaly requires the selection of one of three translator types on each of three cards in the basic interface and the insertion of an EPROM which, itself, may be modularized for the more common instruments.

Finally, because of the universality of the interface, the present invention is economical and adaptable.

DESCRIPTION OF THE INVENTION

1. General Overview

Figure 1:
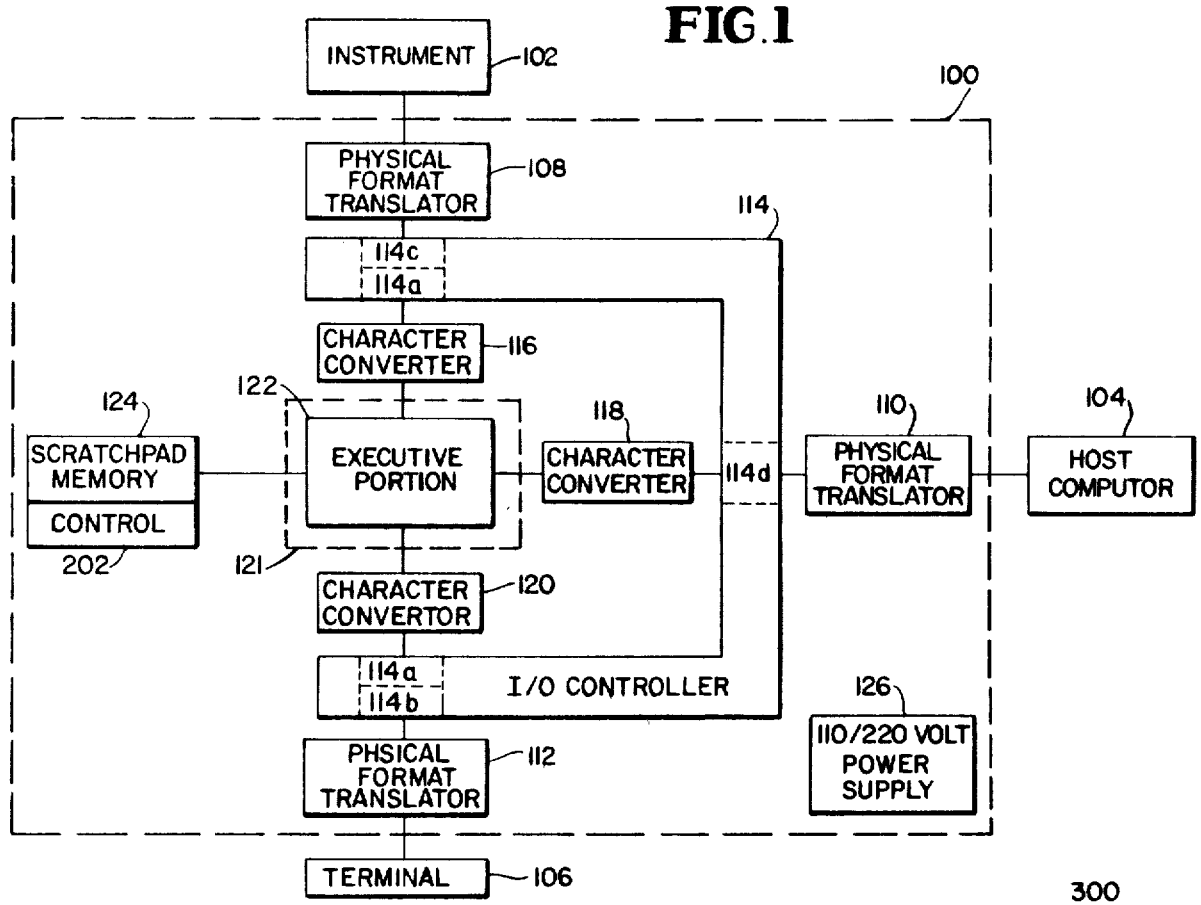
FIG. 1 is a functional block diagram of the interface and environment of the present invention.
Figure 3:
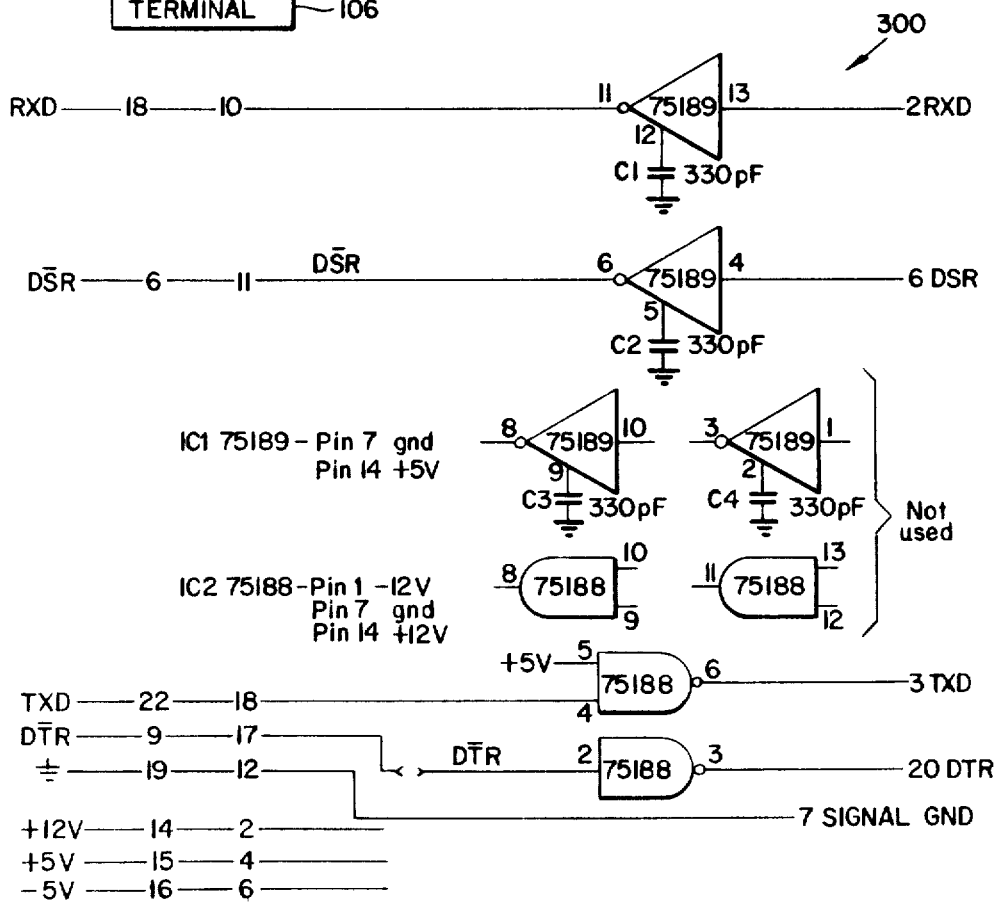
FIGS. 3 through 5 are schematic drawings showing three types of translator elements which change the physical formatting of data.

Referring to FIG. 1, an interface 100 is shown communicatively coupling an instrument 102, a host computer 104, and a terminal 106. The instrument 102 may be any instrument or device which produces a stream of digital data. For example, the instrument 102 may be a blood sample analysis device, such as those currently marketed by Coulter. The instrument 102 may provide its data in any of various physical formats--such as, for example, synchronous or asynchronous RS232, or passive or active current loop, or discrete digital TTL signals. In addition the logical layout of the data stream may be in any of various forms. That is, records of information may be variously arranged into different logical structures for each instrument. Thus, instrument 102 provides digital data which is (a) in any physical format, (b) arranged in a particular logical structure or layout and (c) transmitted according to the particular logic and timing of the instrument 102.

The host computer 104 is a digital processor, such as a commercially available Digital Equipment Corporation PDP 11 computer, which has its own physical format. Similarly, the terminal 106 also has a physical format with which it is compatible.

Perhaps the most common physical format is asynchronous RS232 for ASCII communications. However, numerous currently available instruments, computers, and terminals do not conform to this physical format. Accordingly, the present invention provides translator elements 108, 110 and 112 to account for differences in physical format when such are present. Translator element 108 transforms the digital data outputs from the instrument 102, which is in a first physical format, into corresponding data signals in a common physical format (such as the above-mentioned asynchronous RS232). If the instrument 102 is capable of receiving inputs thereto, the translator element 108 transforms incoming signals in the common physical format into the first physical format with which the instrument 102 is compatible.

Similarly, translator elements 110 and 112 transform signals exiting the host computer 104 and terminal 106, respectively, into the common physical format. Also, signals directed toward the host computer 104 and the terminal 106 in the common physical format are respectively transformed into the physical format with which the host computer 104 or terminal 106 is compatible. Thus, as data enters the interface 100 from the instrument 102, host computer 104, or terminal 106, the data is transformed, if necessary, to conform to the common physical format. Of course, it is noted that the translator elements 108, 110 or 112 may be obviated if the physical format of the instrument 102, the host computer 104, and the terminal 106 originally conform to the common physical format.

Data to and from each translator element 108, 110 and 112 passes through an input/output (I/O) controller 114.

As further noted in FIG. 1, there are three code convertors 116, 118 and 120 associated with the instrument 102, the host computer 104, and the terminal 106, respectively. In addition to the possible discrepancies in physical format which may exist between the instrument 102, the host computer 104, and the terminal 106, a further problem relates to the communication of "prohibited", or unintended function, codes. For example, data characters from the instrument 102, when communicated to the host computer 104, may be interpreted as a control character--such as a CONTROL-C or carriage return. In order to prevent a data character transmitted with one meaning to be misinterpreted by the element receiving the transmission, the convertors 116, 118 and 120 effect a predetermined change of such transmitted characters.

In a first embodiment, all data characters from the instrument 102 which are from 00 through 1F (Hex) in a common ASCII physical format are converted to 40 through 5F (Hex), respectively, to avoid the undesired transmitting of a control character to the host computer 104. In a second embodiment, as discussed later, specifically identified data characters may be converted to other corresponding characters either after transmission by an element or before receipt by an element. In either case, necessary character transformations (e.g. from EBCDIC to ASCII or from control characters to non-control characters) are performed, which change prohibited or inappropriate characters to proper, acceptable characters. It is, of course, noted that the character transformations may be performed in either direction-- from host computer 104 to instrument 102 or from instrument 102 to host computer 104--as appropriate.

The central portion of the interface 100 includes a microprocessor 121 which includes an executive portion 122 for executing instructions entered into the microprocessor 121 from the host computer 104. The executive portion 122 is communicatively connected to the convertors 116, 118 and 120 and to a scratchpad memory 124.

The interface 100 is powered by a conventional power supply 126 which may provide 110 volts or 220 volts as required.

It is noted that the translator elements 110 and 112 and the convertors 118 and 120--for a given host computer 104 and terminal 106--can be incorporated with the executive portion 122 of the interface 100, the incorporated basic unit remaining unchanged regardless of the nature of instrument 102. Hence, to avoid physical format or coding problems introduced by connecting a new instrument to the interface 100, only a translator element 108 and convertor 116 need by changed. Further, of course, if there are no coding incompatibilities, the convertors 116 through 120 be appropriately modified or removed. Translator elements 110, 112 and convertors 118, 120 can be modules facilitating insertion or replacement thereof with different host computers or terminals.

2. Hardware

Figure 2:
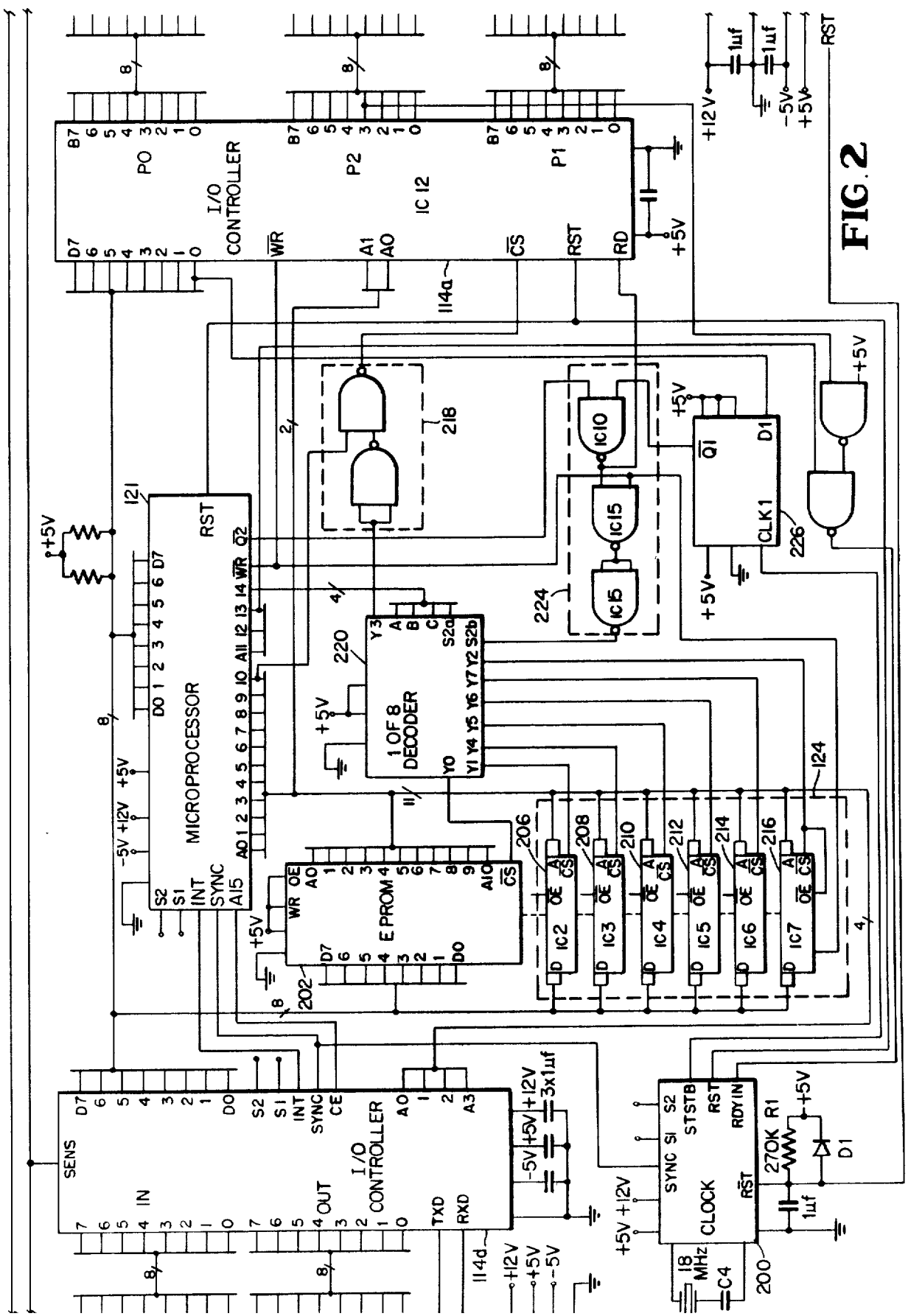
FIG. 2 is a schematic drawing showing the portion of preferred hardware employed by the invention.
Figure 4:
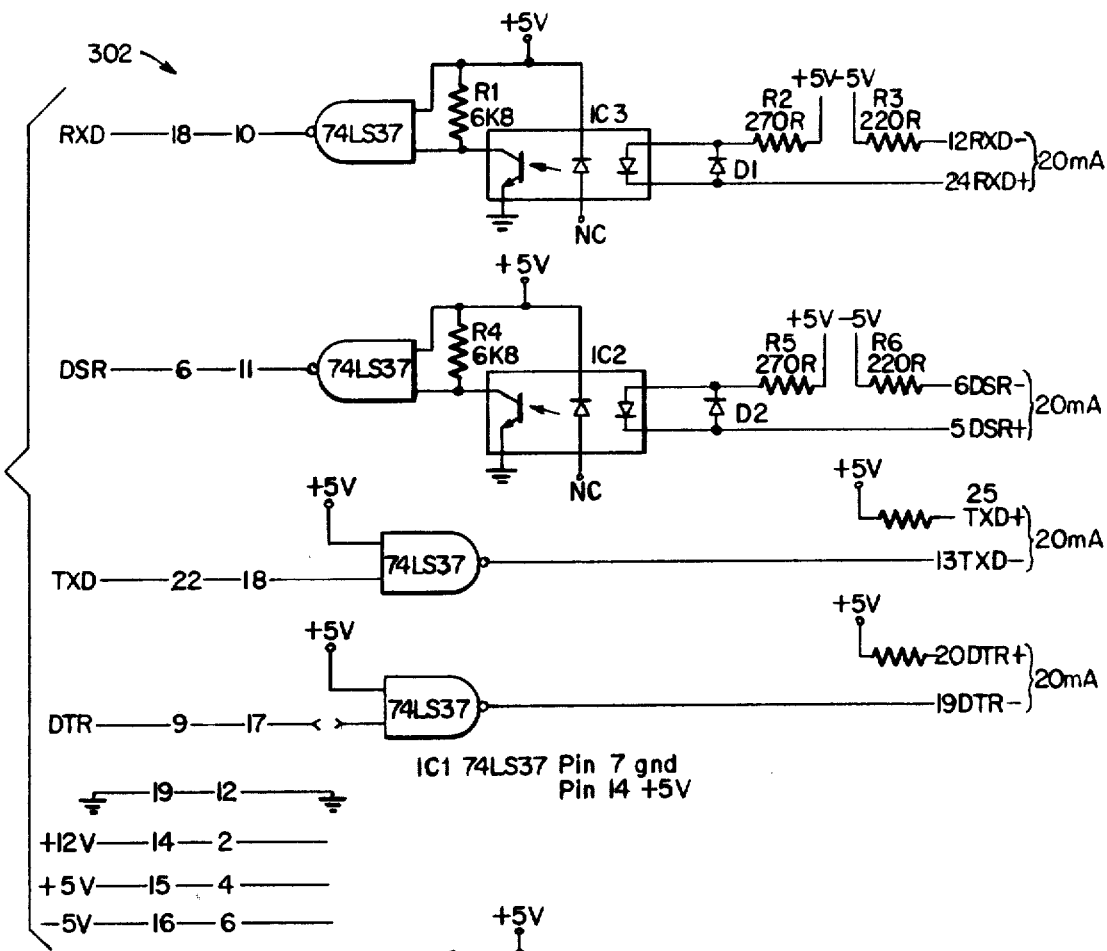
Figure 5:
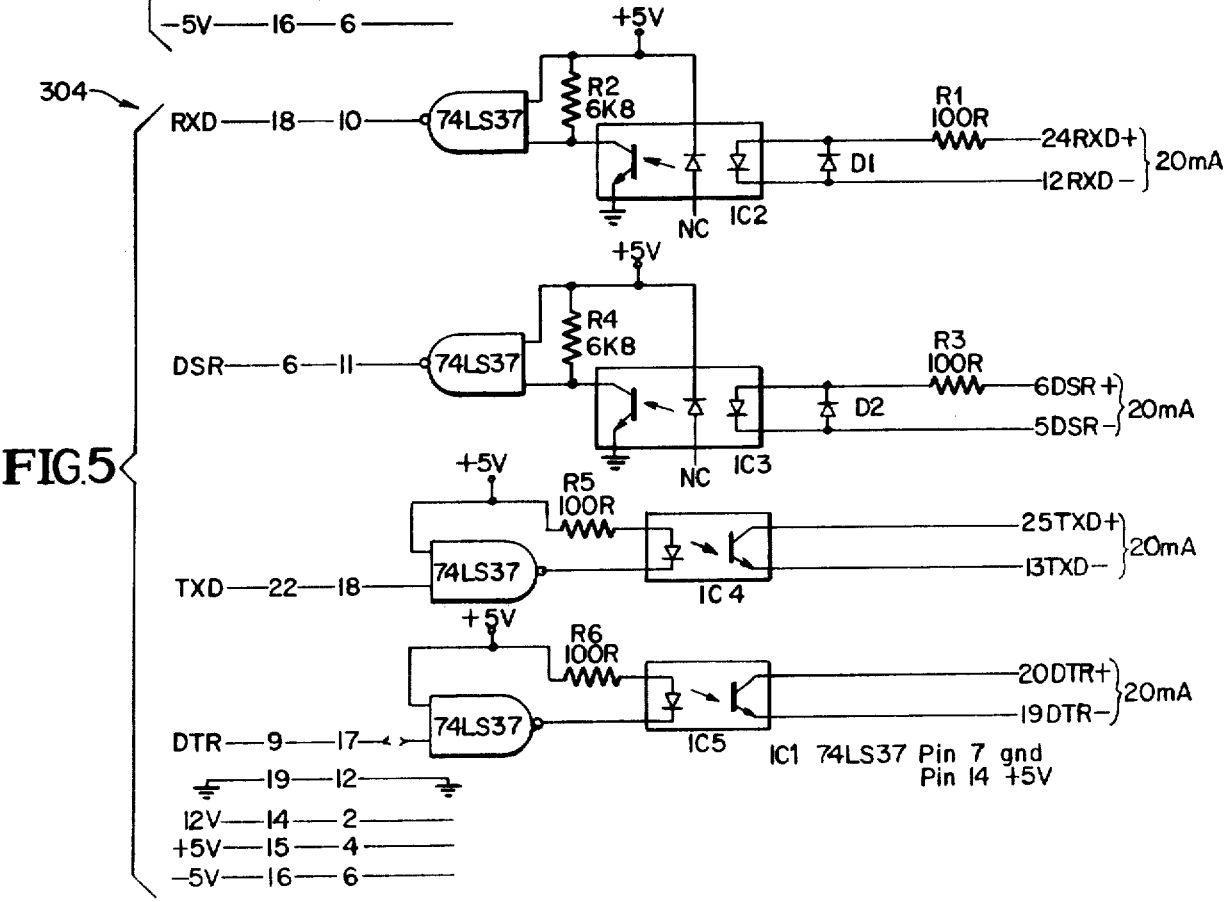

Precise hardware which may be employed in implementing the block diagram of FIG. 1 is shown in FIG. 2 through 6. In FIG. 2, the microprocessor 121 is shown connected to the I/O controller 114 through which the microprocessor 121 communicates with the instrument 102, the host computer 104, and the terminal 106. The microprocessor 121 preferably comprises an Intel P8080A 8-bit n-channel microprocessor (which is shown in FIG. 2), although other microprocessors-- -such as the Zilog Z-80--could be used. The microprocessor 121 is driven by a clock 200, such as an Intel P8224.

The scratchpad memory 124 is shown connected to the microprocessor 121 and to various outputs of the portion 114a of the I/O controller 114 which is connected to the translator element 108 of the instrument 102. In FIG. 2, the data outputs $D_0$ through $D_7$ of the I/O controllers 114d and 114a (TI TMS5501NL and Intel P8255A-5, respectively) are connected to a control element 202--such as a National Semiconductor EPROM MM2716Q--and random access memories 206 through 216 (RAMS)--such as a Hitachi HM611660-3-- -of the scratchpad 124; and microprocessor 121. Lines $D_0$ through $D_7$, in effect, represent the data buss of the interface 100. The $A_0$ through $A_{10}$ address lines of the microprocessor 121 connect to corresponding address lines of the EPROM 202 and the RAMs 206 through 216 of the scratchpad 124. The EPROM control 202; one of the six RAMs 206 through 216 of the scratchpad memory 124; or an input to gate 218 is selected by a one-of-eight decoder 220 which receives as input the address lines $A_{11}$ through $A_{14}$ of the microprocessor 121. The decoder 220 also receives an input from a gating arrangement 224, the output of which is triggered by a flip-flop 226—such as a Fairchild F74LS74PC—and inputs from the microprocessor 121.

FIGS. 2 through 5 show three types of physical compatability translator elements 300, 302 and 304. Element 300 relates to data in the V.24 RS232 mode; element 302 relates to data in current loop active mode; and element 304 relates to data in a current loop passive mode. In each of the translator elements 300, 302 and 304, four signal lines are identifiable. An RXD, TXD, DSR (or $\overline{DSR}$) or DTR (or $\overline{DTR}$) are shown being processed in various conventional ways to achieve a particular physical format.

Figure 6:
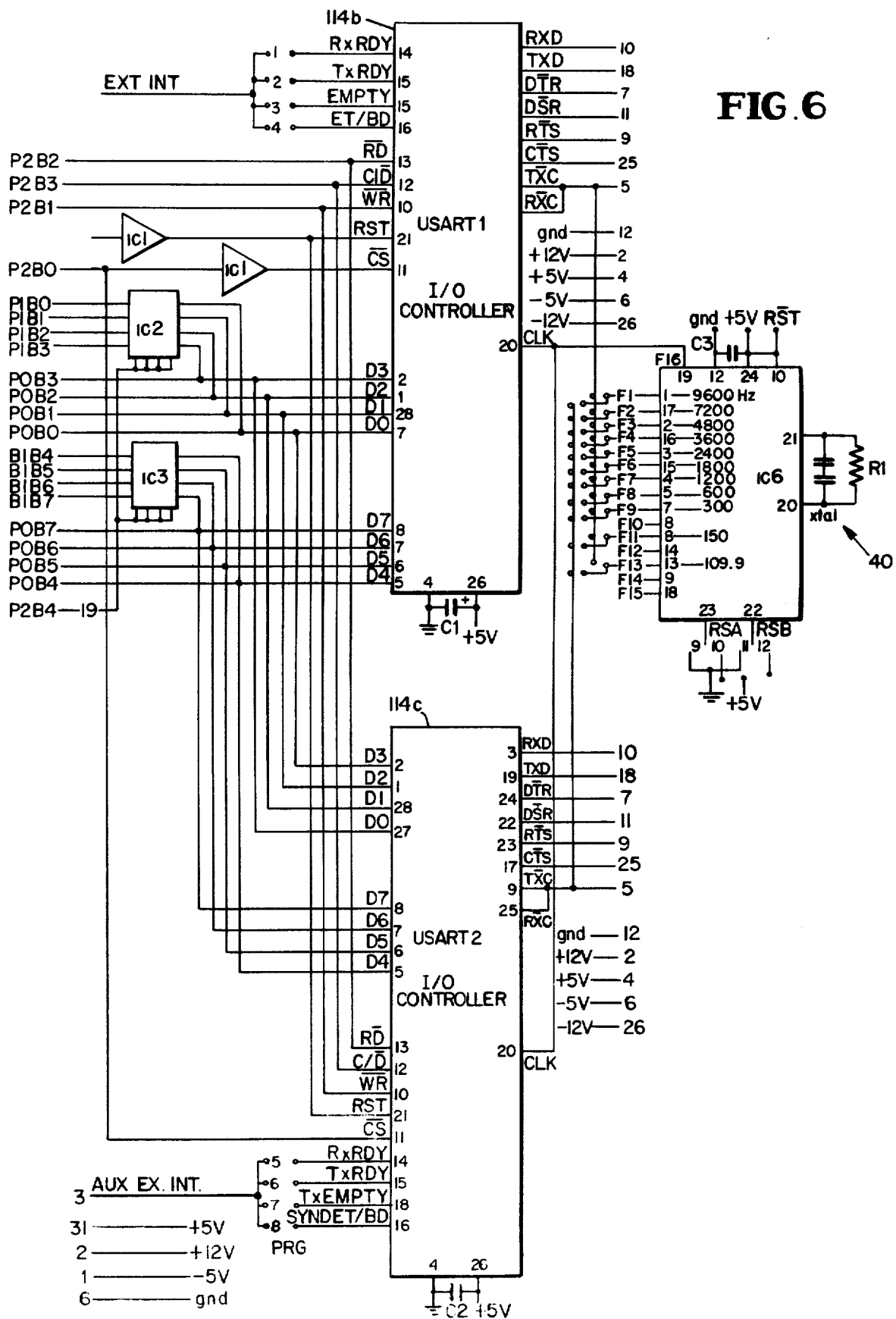
FIG. 6 is a schematic drawing showing an I/O controller portion of preferred hardware of the invention.

Referring now to FIG. 6, it is noted that the four signal lines RXD, TXD, DSR ($\overline{DSR}$), DTR ($\overline{DTR}$) are connected to portions 114b and 114c of the I/O controller 114 at similarly identified pins thereon. Portions 114b and 114c include universal synchronous/asynchronous receiver transmitter (USART) devices, preferably 8251A integrated circuits as shown in FIG. 6. The portions 114b and 114c are connected to three ports $P_0$ (input from 114b and 114c), $P_1$ (output to 114b and 114c), and $P_2$ (control signals to and from 114b and 114c) of portion 114a of the I/O controller 114 (of FIG. 2) as indicated by common designators. For example, pin 27 of a USART 8251A of portion 114b corresponds to data line $D_0$ which is directed to Port 0, line B0 (i.e. pin 4) of the I/O controller portion 114a.

3. Implementation of Hardware

The hardware of FIGS. 2 through 6 is implemented by instructions directed from the host computer 104 to the microprocessor 121. To distinguish instructions from other types of communication with the microprocessor 121, the prefix @@, or $64_{10}$ $64_{10}$ in ASCII, precedes each instruction.

A list of preferred instructions is provided below, indicating the mnemonic, the instruction, and a summary of the action initiated thereby.

| Mnemonic | Instruction | Definition of Action |
| --- | --- | --- |
| @@OD | Open Device | Open a communication channel between the host computer 104 and the instrument 102. All data flowing between these two units will be "filtered" in full-duplex mode. The communication channel is closed when the filter intercepts a @@CL instruction coming from the host computer 104. This allows the operator to communicate directly with the newest laboratory devices which allow input. |
| @@OT | Open Terminal | Open a communication channel between the host computer 104 and the terminal 106. The interface 100 continues to collect data (if @@RU instruction has issued) from the instrument 102 simultaneously. The full-duplex communication between the host computer 104 of the terminal 106 are not "filtered" but are simply monitored in order to detect a @@CL instruction which will close this channel. |
| @@TT | Tie Terminal | Open a communication channel between the instrument 102 and the terminal 106. In this mode the results coming from the instrument 102 are not stored in the scratchpad memory 124 but are sent "as is" to the terminal 106. This communication channel is closed upon receipt of a @@CL instruction from the terminal 106 or the host computer 104. |
| @@CL | CLose | Used to close any above communication channel (only one of which may be open at a time.) |
| @@DW | Disable Wraparound | When the interface 100 fills the scratchpad memory 124 and pointer A reaches its maximum value, further data is not entered. |
| @@EW | Enable Wraparound | When the device pointer reaches its maximum value the next results will be placed in the first "free" record starting with record 1. |
| @@RU | RUn | Start the interface 100 receiving data coming from the instrument 102. The data is put into the scratchpad memory 124 according to the logical structure defined by @@SS, @@SN, @@SF. The data re- |

-continued

| Mnemonic | Instruction | Definition of Action |
| --- | --- | --- |
| | | ceiving continues until receipt of a @@HA instruction. |
| @@HA | HAlt | Stop the interface 100 receiving program. Any data arriving from the instrument 102 after the interface 100 has received this instruction will be ignored. |
| @@SS XXX | Set Size | The scratchpad memory 124 is divided by this instruction into logical records. XXX gives the number of logical records of data to be allocated. By default it is 1 (if instruction @@SS XXX is not issued). |
| @@SN XX ZZ | Set Number of fields | Set the number of fields ZZ in each record XX. If @@SN is not issued all records will contain 1 field. |
| @@SF XX YY | Set Field size | Set-up field XX to contain YY characters. This instruction must be executed for all the fields programmed by @@SN instruction. |
| @@SP XXX | Set device Pointer | Set the pointer A in the scratch pad memory 124 to record XXX which indicates the next position for the interface 100 to place data arriving from the instrument 102. |
| @@ER XXX | ERase Record | Set the host computer 104 pointer (B pointer) to logical record XXX and erase this record. This will set the status of this record to "free". If the record to be erased does not exist the interface 100 will return a @@NA. N.B. One way to clear memory completely is with the @@RE instruction. |
| @@RE | REset | Reset the scratchpad memory 124 to permit a logical restructuring of all records therein. The device pointer ("A" pointer) is set to the 1 position. |
| @@SR XXX | Send Result | Set the host computer pointer B to the logical record XXX and transmit the contents of this record to the host computer 104. If XXX = 0, set the computer pointer B to its previous value plus one, and transmit the contents of that record. If the record does not exist, return a @@NA. If the record is "free", return a @@NR. If the result being returned is the last one in the scratchpad memory 124 which has not been transmitted, the interface 100 responds @@LR instead of @@NA on the next @@SR instruction (if no results have been added by the instrument 102 in the intervening time). |
| @@SA | Send status A (Transmit device pointer.) | Transmit the current value of the pointer A without changing that value. |
| @@SB | Send status B (Transmit host computer pointer.) | Transmit the current value of the host computer pointer B without changing that value. N.B.: Both @@SA and @@SB require that the host computer 104 returns the value it received to check for transmission errors. The interface 100 sends a @@NA or a @@AC. |

| Mnemonic | Instruction | Definition of Action |
|---|---|---|
| @@NA | Negative Acknowledge | The instruction issued by the host computer 104 to the interface 100 could either not be executed or was in fact syntactically incorrect. |
| @@AC | ACknowledge | The instruction issued by the host computer 104 to the interface 100 was executed correctly and the interface 100 is prepared to receive the next instruction. |

As suggested by the definitions of action, the scratchpad memory 124 is divided into a given number of records (@@SS), each record having a specific number of fields (@@SN), with each field having a corresponding number of characters (@@SF) therein. When data from the instrument 102 enters the scratchpad memory 124 in response to a @@RU instruction, the scratchpad memory 124 fills up according to the logical structure defined by the records. If the scratchpad memory 124 continues receiving data after it is filled, the data is disregarded if a @@DW was previously entered or replaces the oldest data in wraparound fashion if the host computer 104 previously provided a @@EW instruction. With a @@HA the stream of data to the interface 100 ceases. A record is erased by a @@ER instruction, while the entire scratchpad memory 124 is erased with a @@RE instruction.

Of particular importance is the @@SR instruction when viewed in conjunction with the @@RU instruction and the instructions relating to dividing the scratchpad memory 124. Together these instructions permit an operator, via an application program stored in the host computer 104, to (a) define the logical structure of the scratchpad memory 124 into records, (b) determine when the data is to be directed to the scratchpad memory 124, and (c) determine when the host computer 104 is to receive the data. The host computer 104 (or terminal 106 connected thereto) is thus in control of how and when data is to be collected.

All instructions which contain an operand, such as XXX or YYY, are retransmitted back to the host computer 104 by the interface 100. This is in lieu of an acknowledge or a not acknowledge signal. If the host computer 104 determines that there has been a transmission error, the instruction is again transmitted by the host computer 104 to the interface 100. When data originates at the interface 100, as results from an @@SR instruction, the interface 100 expects that the host computer 104 will retransmit the data upon which the interface 100 responds @@AC or @@NA—indicating an acknowledgement or nonacknowledgement—as appropriate. It is up to the operator to re-request records which have had transmission errors. The last character of a record will be a digit added by the interface 100. The added digit is 0 if the data received by the interface 100 was received (a) without any problem or (b), if the data is a check sum or other control, the check sum or other control was correct. The added digit is 1 if the data (a) was not reliably received from the instrument 102 or (b) if the check sum or other control was not correct upon reception from the instrument 102.

A preferred manner in which the instructions implement the hardware of FIGS. 2 through 6 is set forth in the accompanying flowchart of Table I and microprocessor program of Table II. In the flow chart and the program, the term "device" is interchangeable with instrument 102 and the terms "host" and "computer" refer to the host computer 104. The flow chart and program are in the original application file.

Worthy of special note, the RECEPTION INTERRUPT FROM THE DEVICE includes a decision statement "is the character [sent from the instrument] a control character (00 Hex to 1F Hex in ASCII)?" If so, the character is changed to an alphanumeric character from 40 Hex to 5F Hex. As an alternative, it should be noted, a similar end is achievable by defining instructions, for example @@CI XXX YYY which permit the operator to specify each individual "prohibited" character XXX which should be changed to character YYY automatically before input to the host computer 104. This is readily achieved by a read-only memory or other such look-up table device. Similarly, a @@CO XXX YYY instruction could effect automatic change of each character XXX to YYY when output from the host computer 104.

Also worth noting in the RECEPTION INTERRUPT FROM THE DEVICE are optional interchanges with the instrument 102, for example acknowledgements (ACK) and nonacknowledgements (NAK) which are provided to instruments or devices which have input capabilities. Similarly, a check sum method of confirming data transfer accuracy from the instrument 102 is provided with appropriate instruments.

The present invention is thus readily adaptable for use with numerous instruments and laboratory devices ranging in complexity from "transmit data only" devices to "transmit, receive, and check transmission" type devices.

Further, it should be noted that the invention may be easily enhanced in various ways. First, by expanding the scratchpad memory 124 by including external memory, such as a disc. Second, data from the host computer 104 may—with a proper instruction—be entered and stored in the scratchpad memory 124 by action of the microprocessor 121. If lost from the memory of the host computer 104, the data could be recovered from the scratchpad memory 124. Third, each of a plurality of n interfaces (like 100) may be connected to a corresponding instrument (like 102). Instead of connecting each of the n interfaces to a terminal, however, the n interfaces are all coupled to another interface which is connected to a terminal and host computer. The n interfaces are, in effect multiplexed to the one interface permitting the one interface to communicate with a plurality (n) of instruments.

Also, in accordance with the present invention, it is contemplated that the three types of physical format translators 300, 302 and 304 be included on a single card, any one of which may be selected as desired. One such card may be interposed between the host computer 104 and the I/O Controller 114; another such card may be interposed between the instrument 102 and the I/O controller 114; and a third card may be interposed between the terminal 104 and the I/O Controller 114. Each of the three physical format translators 108, 110 and 112 can thus selectively perform, as desired, one of the three (or more, if provided) translation options. For example, a particular one of the three physical format translations may be selected for a corresponding host computer.

Still further, it is noted that the present invention may operate in a basic embodiment without the terminal 106.

That is, instructions from the host computer 104 and data sent from the instrument 102 form the basic external environment for the interface 100. However, including the terminal greatly enhances the invention by adding to the operator's interactive role in the overall process of data transfer.

Finally, although three instructions are normally provided in dividing up the scratchpad memory 124, it is also within the teachings of the invention to divide the scratchpad memory 124 by any number of instructions greater than one. Similarly, other actions may be achieved by adding or modifying the instructions within the teachings of the invention.

Other improvements, modifications and embodiments will become apparent to one of ordinary skill in the art upon review of this disclosure. Such improvements, modifications and embodiments are considered to be within the scope of this invention as defined by the following claims.

I claim:

1. In a communication system having a digital host computer and an instrument which generates a stream of serial digital outputs, a universal communication interface coupled between the host computer and the instrument, the interface comprising:
    a microprocessor having executive means for executing instructions entered by the host computer into the microprocessor, the instructions forming a set of distinct instructions; and
    a scratchpad memory for receiving and storing digital signals;
    wherein the executive means divides the scratchpad memory into a defined structure of at least one record in response to the receiving of at least one corresponding instruction having a selectable variable portion from the host computer, the selected variable portion determining the defined structure of the scratchpad memory and wherein digital signals, corresponding to the digital outputs from the instrument, are directed into and in conformance with the defined structure of one of the at least one record in response to a corresponding instruction from the host computer.

2. An interface according to claim 1 wherein the instrument is coupled to the scratchpad memory by a first channel and wherein the first channel is selectively closed by the executive means in response to a corresponding instruction entered by the host computer.

3. An interface according to claim 2 wherein the host computer communicates digital data in a first physical format and the instrument communicates digital data in a second physical format, the interface further comprising:
    physical compatibility means for (a) conforming all digital signals entering the interface from the computer and the instrument into a standard physical format compatible with the microprocessor means and (b) conforming the digital signals exiting the interface into the first physical format or the second physical format depending on whether the host computer or the instrument, respectively, is the destination of the exiting signals.

4. An interface according to claim 3 wherein the first physical format differs from the standard physical format and the second physical format differs from the standard physical format, and wherein the physical compatibility means comprises:
    a first translator element connected between the executive means and the instrument, the first translator element changing the physical format of digital signals communicated to and from the instrument to effect physical compatibility, and
    a second translator element connected between the executive means and the host computer, the second translator element changing the physical format of digital signals communicated to and from the host computer to effect physical compatibility.

5. An interface according to claim 1 further comprising:
    means for converting prohibited digital data characters from the instrument into digital characters which are allowed inputs to the host computer.

6. An interface according to claim 4 further comprising:
    means for converting prohibited digital data characters from the instrument into digital characters which are allowed inputs to the host computer.

7. An interface according to claim 5 wherein the converting means changes any digital character which corresponds to a control character in the host computer into a digital character which does not correspond to a host computer control character.

8. An interface according to claim 3 wherein the common physical format is asynchronous ASCII and wherein distinct instructions includes a multi-character mnemonic which includes a two character prefix, wherein the two-character prefix is @@ which represents $64_{10} 64_{10}$ in ASCII.

9. An interface according to claim 4 wherein the second translator element is incorporated with the executive means into a single unit.

10. An interface according to claim 6 further comprising:
    means for selectively deleting portions of digital output from the intstrument.

11. An interface according to claim 10 wherein the converting means and the deleting means comprise programmable ready-only memory (PROM) which is adapted to each distinct instrument coupled to the interface.

12. An interface according to claim 1 wherein the scratchpad memory temporarily stores the digital signals corresponding to the digital outputs from the instrument, the digital signals in the stratchpad memory being directed toward the host computer in response to a corresponding instruction by the host computer to the microprocessor means.

13. An interface according to claim 10 wherein the scratchpad memory temporarily stores the digital signals corresponding to the digital outputs from the instrument, the digital signals in the scratchpad memory being directed toward the host computer in response to a corresponding instruction by the host computer to the microprocessor means.

14. An interface according to claim 12 wherein the scratchpad memory comprises random access memory (RAM).

15. An interface according to claim 1 wherein digital signals entering the scratchpad memory wraparound once the scratchpad memory is filled.

16. An interface according to claim 1 wherein digital signals entering the scratchpad memory do not wraparound once the scratchpad memory is filled.

17. An interface according to claim 1 wherein digital signals entering the scratchpad memory either (a) wraparound or (b) do not wraparound once the scratchpad memory is filled, the wraparound mode being established by the executive means in response to one corresponding instruction from the host computer and the not wraparound mode being established by the executive means in response to a differing corresponding instruction from the host computer.

18. An interface according to claim 13 wherein digital signals entering the scratchpad memory either (a) wraparound or (b) do not wraparound once the scratchpad memory is filled, the wraparound mode being established by the executive means in response to one corresponding instruction from the host computer and the not wraparound mode being established by the executive means in response to a differing corresponding instruction from the host computer.

19. A interface according to claim 1 wherein each record in the scratchpad memory has an indentifier applied thereto by the microprocessor in response to a corresponding instruction from the host computer.

20. An interface according to claim 18 wherein each record in the scratchpad memory has an identifier applied thereto by the microprocessor in response to a corresponding instruction from the host computer.

21. An interface according to claim 1 wherein the microprocessor points to a record with a particular identifier in response to a corresponding instruction from the host computer.

22. An interface according to claim 1 wherein each of the at least one records has at least one field, and each field has at least one digital character therein; and wherein:
   (a) the number of records,
   (b) the number of fields in each record, and
   (c) the number of digital characters in each field
are each determined by the microprocessor in response to a respective instruction from the host computer.

23. An interface according to claim 10 wherein each of the at least one records has at least one field, and each field has at least one digital character therein; and wherein:
   (a) the number of records,
   (b) the number of fields in each record, and
   (c) the number of digital characters in each field
are each determined by the microprocessor in response to a respective instruction from the host computer.

24. An interface according to claim 20 wherein each of the at least one records has at least one field, and each field has at least one digital character therein; and wherein:
   (a) the number of records,
   (b) the number of fields in each record, and
   (c) the number of digital characters in each field
are each determined by the microprocessor in response to a respective instruction from the host computer.

25. An interface according to claim 1 wherein the microprocessor comprises first handshaking means for directing digital outputs from the host computer back to the host computer for acknowledgement.

26. An interface according to claim 1 wherein the microprocessor means comprises second handshaking means for directing digital outputs from the instrument back to the instrument for accuracy checking.

27. An interface according to claim 25 wherein the microprocessor comprises second handshaking means for directing digital outputs from the instrument back to the instrument for accuracy checking.

28. In a communication system having a digital host computer and an instrument which generates a stream of serial digital outputs to be processed by the host computer, and interface communicatively coupled between the host computer and the instrument, the interface comprising:
   a microprocessor having executive means for executing instructions entered one at a time by the host computer into the microprocessor;
   means for controlling the timing of communication of the digital outputs to the host computer, the controlling means comprising a scratchpad memory means for storing digital outputs from the instrument in response to a corresponding instruction to the executive means from the host computer, the digital outputs stored in the scratchpad memory means communicated to the host computer in response to a corresponding instruction to the executive means from the host computer; and
   means for converting prohibited digital data characters from the instrument into digital characters which are allowed inputs to the host computer.

29. An interface according to claim 28 further comprising:
   physical compatibility means for (a) conforming all digital signals entering the interface from the host computer and the instrument into a standard physical format compatible with the microprocessor means and (b) conforming the digital signals exiting the interface into the physical format corresponding to either the host computer or the instrument, respectively, whichever is the destination of the exiting signals.

30. An interface according to claim 28 wherein the microprocessor in response to at least one selectable variable instruction from the host computer, correspondingly selectively divides the scratchpad memory means into a plurality of records and wherein the microprocessor, in response to a corresponding instruction from the host cmputer, directs digital signals, corresponding to the digital outputs from the instrument, into one record after another,
   the digital signals thereby being communicated to the host computer in the form of records initially defined by the host computer.

31. In a communication system having a digital host computer, a terminal, and an instrument which generates a stream of serial digital outputs to be processed by the host computer, an interface communicatively coupled between the host computer, the terminal, and the instrument, the interface comprising:
   a microprocessor having executive means for executing instructions entered one at a time by the host computer into the microprocessor;
   means for controlling the timing of communication of the digital outputs to the host computer in response to a corresponding instruction to the executive means from the host computer, the controlling means comprising a scratchpad memory means for receiving and storing digital signals which correspond to the digital outputs from the instrument, the digital outputs stored in the scratchpad memory means being communicated to the host computer in response to a corresponding instruction to the executive means from the host computer;

physical compatibility means for (a) conforming all digital signals entering the interface from the host computer, the terminal, and the instrument into a standard physical format compatible with the microprocessor means and (b) conforming the digital signals exiting the interface into the physical format corresponding to either the host computer, the terminal, or the instrument, respectively, whichever is the destination of the exiting signals;

means for converting prohibited digital data characters from the instrument into digital characters which are allowed inputs to the host computer; and means for converting to digital data characters required by the instrument, characters which are normally prohibited to be out from the host computer.

32. An interface according to claim 31 further comprising:

a first communication channel between the host computer and the terminal;

a second communication channel between the host computer and the instrument; and a third communication channel between the terminal and the instrument;

wherein the executive means opens a selected one of the three channels in response to a corresponding respective instruction from the host computer to the executive means, no more than one channel being open at any time; and wherein the executive means is transparent to communications between the host computer and the terminal when the first communication channel is open.

33. An interface according to claim 32 wherein the executive means executes a closing of all three channels in response to a corresponding instruction from the host computer to the executive means.

34. An interface according to claim 22 wherein in each of the three channels is a full duplex communication channel.

35. An interface according to claim 32 wherein digital signals can be received and stored in the scratchpad memory means in response to the corresponding instruction from the host computer at least substantially simultaneous with communications between the host computer and the terminal when the first channel is open in response to the corresponding instruction from the host computer.

36. A method of interfacing by means of a microprocessor (a) an instrument which provides a series of digital outputs and (b) a digital host computer, the method comprising the steps of:

interposing a scratchpad memory between the instrument and the host computer;

forming a set of distinct instructions executable by the microprocessor;

transmitting a first number of the instructions from the host computer to the microprocessor whereupon the microprocessor executes the first number of instructions by dividing the scrathpad memory into a plurality of records;

transmitting a second number of the instructions from the host computer to the microprocessor whereupon the microprocessor executes the second number of instructions by entering digital signals, which correspond to the digital outputs from the instrument, into one record after another; and transmitting a third number of the instructions from the host computer to the microprocessor whereupon the microprocessor executes the third number of instructions by directing the digital signals entered into the records toward the host computer;

whereby the transmission and execution of the first number of instructions, the second number of instructions, and the third number of instructions in sequence results in the host computer controlling the time at which the host computer is to receive digital inputs corresponding to the digital outputs from the instrument;

the first, second, and third number of instructions each including at least one instruction.

37. A method as in claim 36 wherein the host computer processes digital data in a physical format which differs from the physical format in which the intrument processes, the method comprising the further steps of:

conforming all digital outputs from the host computer and the instrument to a standard physical format;

conforming the digital inputs to the host computer to the physical format compatible therewith; and conforming the digital inputs to the instrument to the physical format compatible therewith, thereby avoiding physical incompatibilites between the host computer and the instrument.

38. A method according to claim 36 wherein certain digital characters provided as output by the instrument represent digital characters which the host computer should not receive, the method comprising the further step of;

automatically converting the digital characters which the host computer should not receive into digital characters which are receivable by the host computer, thereby avoiding coding incompatibilities between the host computer and the instrument.

39. A method according to claim 37 wherein certain digital characters provided as output by the instrument represent digital characters which the host computer should not receive, the method comprising the further step of:

automatically converting the digital characters which the host computer should not receive into digital characters which are receivable by the host computer, thereby avoiding coding incompatibilities between the host computer and the instrument.

40. A method according to claim 6 wherein the first translator element and the converting means comprise a programmable read-only memory.

41. An interface according to claim 1 further comprising:

means for converting normally prohibited digital data characters from the host computer into digital characters which are required inputs to the instrument.

42. An interface according to claim 5 wherein the converting means changes any digital character which does not correspond to a control character in the instrument into a digital character which corresponds to a required instrument control character.

43. An interface according to claim 31 further comprising:

means for converting prohibited digital data characters from the host computer into digital characters which are allowed inputs to the instrument.

44. A method according to claim 38 comprising the further step of:

automatically converting the digital characters which the host computer normally may not transmit into digital characters which are required by the instrument.

45. An interface according to claim 10 wherein the deleting means comprise programmable read-only memory (PROM) which is adapted to each distinct instrument coupled to the interface.

46. An interface according to claim 10 wherein the converting means comprise programmable read-only memory (PROM) which is adapted to each distinct instrument coupled to the interface.

47. An interface according to claim 14 wherein the scratchpad memory further comprises an external memory.

48. An interface according to claim 3 wherein the first physical format differs from the standard physical format and the second physical format differs from the standard physical format, and wherein the physical compatibility means comprises:

a first card having a plurality of common types of translator elements thereon and a second card having a plurality of common types of translator elements thereon;

wherein a first translator element selected from the first card is connected between the executive means and the instrument, the first translator element changing the physical format of digital signals communicated to and from the instrument to effect physical compatibility; and wherein a second translator element selected from the second card is connected between the executive means and the host computer, the second translator element changing the physical format of digital signals communicated to and from the host computer to effect physical compatibility.

* * * * *